United States Patent
Stank et al.

(10) Patent No.: US 9,855,088 B2
(45) Date of Patent: Jan. 2, 2018

(54) TORQUE LIMITING INSTRUMENT

(71) Applicant: DePuy Synthes Products, Inc., Raynham, MA (US)

(72) Inventors: Bernd Stank, Grenchen (CH); Silas Zurschmiede, Grenchen (CH); Konrad Schaller, Grenchen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 324 days.

(21) Appl. No.: 14/598,530

(22) Filed: Jan. 16, 2015

(65) Prior Publication Data

US 2015/0201986 A1    Jul. 23, 2015

Related U.S. Application Data

(60) Provisional application No. 61/928,662, filed on Jan. 17, 2014.

(51) Int. Cl.
| | |
|---|---|
| *A61B 17/88* | (2006.01) |
| *B25B 15/04* | (2006.01) |
| *B25B 23/142* | (2006.01) |
| *B25B 15/02* | (2006.01) |
| *A61B 90/00* | (2016.01) |

(52) U.S. Cl.
CPC ...... *A61B 17/8888* (2013.01); *A61B 17/8875* (2013.01); *A61B 17/8894* (2013.01); *A61B 90/03* (2016.02); *B25B 15/02* (2013.01); *B25B 23/1427* (2013.01); *A61B 2090/031* (2016.02)

(58) Field of Classification Search
CPC .. B25B 15/04; B25B 23/1427; A61B 17/8875
See application file for complete search history.

(56) References Cited

U.S. PATENT DOCUMENTS

| 176,811 | A | * | 5/1876 | Richards | ................. B25B 15/04 |
|---|---|---|---|---|---|
| | | | | | 192/44 |
| 666,512 | A | * | 1/1901 | Furbish | ................... B25B 15/04 |
| | | | | | 81/29 |
| 2,439,980 | A | * | 4/1948 | Livermont | .......... B25B 23/1427 |
| | | | | | 267/158 |
| 3,157,258 | A | | 11/1964 | Cronholm | |
| 4,249,435 | A | * | 2/1981 | Villeneuve | .......... B25B 23/1427 |
| | | | | | 81/477 |
| 4,687,392 | A | | 8/1987 | Bidwell | |
| 5,002,555 | A | | 3/1991 | Petersen | |
| 5,507,211 | A | | 4/1996 | Wagner | |
| 5,615,587 | A | | 4/1997 | Foerster, Jr. | |

(Continued)

FOREIGN PATENT DOCUMENTS

| DE | 3140288 A1 | 4/1983 |
|---|---|---|
| DE | 3149561 A1 | 6/1983 |

(Continued)

OTHER PUBLICATIONS

U.S. Appl. No. 61/928,662, filed Jan. 17, 2014, Stank et al.

(Continued)

*Primary Examiner* — Nicholas Woodall
(74) *Attorney, Agent, or Firm* — Baker & Hostetler LLP (57) ABSTRACT

A torque limiting instrument can is configured to drive a shaft to rotate in a select direction in response to an applied torque until the applied torque reaches a predetermined threshold.

20 Claims, 5 Drawing Sheets

(56) References Cited

U.S. PATENT DOCUMENTS

| | | |
|---|---|---|
| 6,990,877 B1 | 1/2006 | Wu |
| 7,484,440 B2 | 2/2009 | Wright |
| 8,136,431 B2 | 3/2012 | Wengreen |
| 8,172,003 B2 | 5/2012 | Robieu et al. |
| 2005/0072277 A1 | 4/2005 | Knox et al. |
| 2010/0055978 A1 | 3/2010 | Montena |
| 2011/0162492 A1 | 7/2011 | Wilson et al. |
| 2015/0252855 A1* | 9/2015 | Jakoubek ................ F16D 7/048 464/37 |

FOREIGN PATENT DOCUMENTS

| | | |
|---|---|---|
| DE | 3413761 A1 | 10/1985 |
| DE | 3808238 A1 | 10/1988 |
| DE | 4022763 A1 | 1/1991 |
| DE | 20314010 U1 | 1/2005 |
| DE | 102007051263 | 4/2009 |
| DE | 102011052442 B3 | 9/2012 |
| EP | 0019019 A1 | 11/1980 |
| EP | 1092510 B1 | 12/2009 |
| EP | 2023840 B1 | 1/2011 |
| GB | 319355 A | 8/1930 |
| GB | 599547 A | 3/1948 |
| WO | WO 02/097386 | 12/2002 |

OTHER PUBLICATIONS

U.S. Appl. No. 61/928,713, filed Jan. 17, 2014, Schaller et al.
U.S. Appl. No. 61/928,691, filed Jan. 17, 2014, Voisard et al.
U.S. Appl. No. 14/598,597, filed Jan. 16, 2015, Schaller et al.

\* cited by examiner

TORQUE LIMITING INSTRUMENT

CROSS-REFERENCE TO RELATED APPLICATIONS

This claims priority to U.S. Patent Application Ser. No. 61/928,662 filed Jan. 17, 2014, the disclosure of which is hereby incorporated by reference as if set forth in its entirety herein.

BACKGROUND

Surgical securement devices, such as surgical anchors, that fix implants to bone or other tissue are effective when used consistently with clinically tested protocols. In one example, surgical anchors configured as surgical screws that are rotatably driven through an implant and into a target surgical location so as to fix the implant to the target surgical location. Surgical screws can be configured as bone screws that are driven through the implant, whereby the target surgical location is bone. Torque limiters are one type of device that surgeons can use to help position and appropriately lock the surgical anchor in place. Torque limiters can help ensure that no more than a desired torque is applied to the surgical anchor during implantation. Despite the use of torque limiters for medical applications, typical torque limiter designs are complex and costly to manufacture.

SUMMARY

In accordance with one embodiment, a torque instrument can include a shaft having a driving end, a hub rotatably fixed with respect to the shaft, and a displaceable member that is spaced radially with respect to the hub and rotatably fixed with respect to the hub. The torque limiting surgical screw driver can further include a deformable gasket disposed between the displaceable member and the hub, and a cover that extends about the displaceable member such that the displaceable member is disposed between the cover and the deformable gasket. The cover can be rotatably coupled to the displaceable members with respect in a first direction of rotation until a torque applied to the cover in the first direction of rotation reaches a predetermined threshold, at which point the cover causes the displaceable member to bias the deformable gasket to deform a sufficient distance such that the cover becomes rotatably decoupled from the displaceable members in the first direction of rotation.

BRIEF DESCRIPTION OF THE DRAWINGS

The foregoing summary, as well as the following detailed description of illustrative embodiments of the instrument of the present disclosure, will be better understood when read in conjunction with the appended drawings. It should be understood, however, that the application is not limited to the precise schematics and arrangements shown. In the drawings.

DETAILED DESCRIPTION

Figure 1:
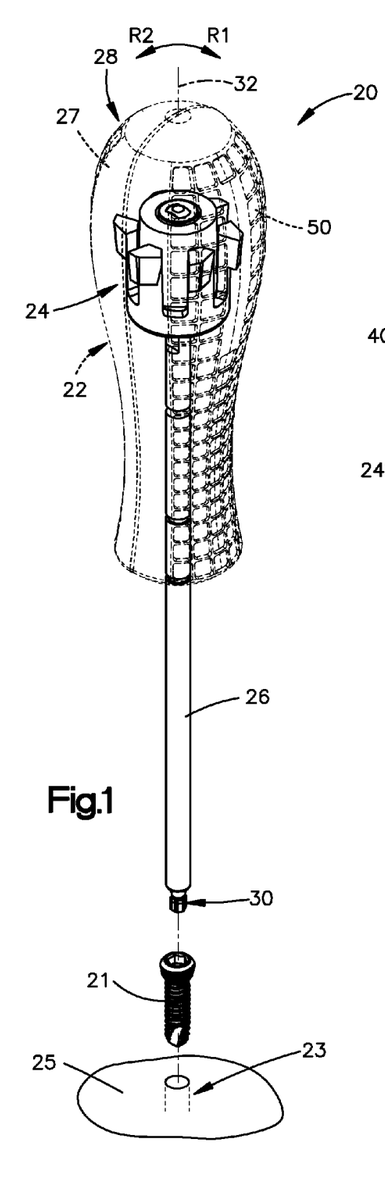
FIG. 1 is a perspective view of a torque limiting instrument constructed in accordance with one embodiment, showing certain portions as transparent for illustrative purposes.
Figure 2:
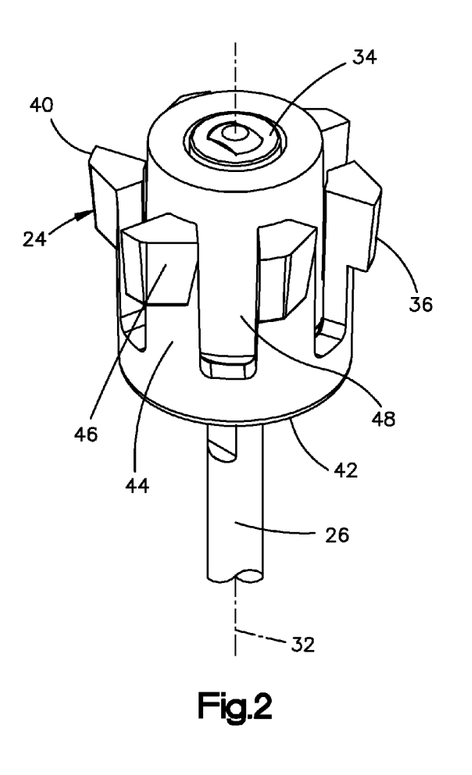
FIG. 2 is a perspective view of a portion of the torque limiting instrument illustrated in FIG. 1, showing a shaft, a cap, and a deformable gasket.

Referring to FIG. 1, a torque limiting instrument 20 can be configured a driver that is configured to receive, be received by, or otherwise support or engage an anchor 21 and rotate the anchor so as to secure the anchor 21 to a target location 23. Thus, it should be appreciated that the anchor 21 can be configured as a screw. The target location 23 can be a target surgical location, and thus the anchor can be referred to as a surgical anchor. Thus, the instrument 20 can also be referred to as a torque limiting surgical screw driver in one configuration. In one application, the target surgical location is bone 25, and the surgical anchor can be referred to as a bone anchor. As will be described in more detail below, the instrument 20 is configured to apply no more than a predetermined torque to the anchor as the driver secures the anchor to the target location. Alternatively, the instrument 20 can be configured as a drill that is configured to create an opening in the target location 23.

The instrument 20 can include a handle 22, a torque transfer assembly 24 in communication with the handle 22, and a shaft 26 supported by the torque transfer assembly 24. The handle 22, the torque transfer assembly 24, and the shaft 26 can be made from a biocompatible plastic, metal, or any suitable alternative biocompatible material as desired unless otherwise indicated below. The handle 22 can define a grip member 27 that defines a proximal end 28 of the instrument 20. The instrument 20 can further define a distal end 30 that is spaced from the proximal end 28 along an axis 32 of the instrument 20. The axis 32 can extend along a longitudinal direction L or any other linear or nonlinear direction as desired. As used herein, the term "proximal" and derivatives thereof refer to a direction from the distal end 30 toward the proximal end 28. As used herein, the term "distal" and derivatives thereof refer to a direction from the proximal end 28 toward the distal 30 end. The distal end 30 can be defined by the shaft 26 at a driving end of the shaft 26 that is configured to support the anchor so as to drive the anchor 21 into the target location 23 or otherwise support a drill bit or define a drill bit that is configured to create an opening in the target location.

The shaft 26 is elongate relative to the handle 22 along the axis 32 to the distal end 30. In accordance with one embodiment, the axis 32 can be defined by a central axis of the shaft 26. When a torque applied to the handle 22 in a first direction of rotation R1 is less than a predetermined threshold, an entirety of the applied torque is transferred through the torque transfer assembly 24 to the shaft 26 and thus to the anchor 21 that is supported by the shaft 26, such that the instrument 20 drives the anchor 21 into the target location 23. For instance, the torque can be applied to the grip member 27. The application of the torque can, for instance, be about the axis 32.

When the torque applied to the handle 22 in the first direction of rotation R1 is greater than the predetermined threshold, the force transfer assembly 24 causes the handle to rotate relative to the shaft 26. Accordingly, the instrument 20 prevents torque greater than the predetermined threshold from being transferred to the shaft 26, and thus to the anchor 21 that is supported by the shaft 26. It will therefore be appreciated that the torque transfer assembly 24 prevents torque greater than the predetermined threshold from being transferred from the handle 22 to the shaft 26, and thus from the handle 22 to the anchor 21 that is supported by the shaft 26. The predetermined threshold can be defined by the torque transfer assembly 24 as described in more detail below.

Referring now to FIGS. 1-4A, the torque transfer assembly 24 includes a hub 34 that is rotatably fixed with respect to the shaft 26, and at least one displaceable member 36 that is spaced radially outward with respect to the hub 34 so as to define a gap 38 between the hub 34 and the displaceable member 36. For instance, the torque transfer assembly 24 can include a plurality of displaceable members 36 that are spaced radially outward with respect to the hub 34 so as to define a gap 38 between the hub 34 and the displaceable member 36. Adjacent ones of the displaceable members 36 can be spaced circumferentially equidistantly from each other or variably from each other. It should be appreciated that the term "radial" and derivatives thereof refer to a direction that is angularly offset, for instance perpendicular, with respect to the axis 32. For instance, the term "radially outward" and derivatives thereof can refer to a direction that is directed away from the axis 32, and can be aligned with the axis 32 or can be offset from the axis 32. The term "radially inward" and derivatives thereof can refer to a direction that is directed toward the axis 32, and can be aligned with the axis 32 or can be offset from the axis 32. The displaceable members 36 are rotatably fixed with respect to the hub 34. Accordingly, rotation of the displaceable members causes the hub 34 to similarly rotate. In accordance with the illustrated embodiment, the hub 34 defines an aperture 35 that receives the shaft 26. For example, the aperture 35 of the hub 34 and the shaft 26 can be noncircular in radial cross section, such that the hub 34 is rotatably coupled to the shaft 26. It should be appreciated, of course, that the hub 34 can be rotatbaly coupled to the shaft 26 in accordance with any suitable embodiment as desired.

As will be described in more detail below, the displaceable members 36 are configured to rotate about the axis 32, which causes the hub 34 to similarly rotate about the axis 32. In accordance with one embodiment, the torque transfer assembly 24 can include a cap 40 that includes the hub 34 and the displaceable members 36 that are monolithic with the hub 34. For instance, the cap 40 can include a seat 42 that is connected between the hub 34 and the plurality of displaceable members 36. As a result, the gap 38 can be open at a first end, such as a proximal end, and can be closed at a second end by the seat 42. The first end can be a proximal end of the gap 38, and the second end can be a distal end of the gap 38. Alternatively, the first end can be a distal end of the gap 38, and the second end can be a proximal end of the gap 38.

It should be appreciated that the hub 34, the seat 42, and the displaceable members 36 can be monolithic with each other. Alternatively, the displaceable members 36 can be rotatably coupled to the hub 34 in accordance with any suitable embodiment as desired. The displaceable members 36 can, for instance, extend from the seat 42, and can be deflectable with respect to the seat 42 in the radial direction toward the axis 32. For instance, the displaceable members 36 can be elastically deflectable with respect to the seat 42 in the radial direction toward the axis 32. As illustrated at FIG. 5C, the displaceable members 36 can each define a stem 44 that extends from the seat 42, and an engagement member 46 that is supported by the stem 44. The stem 44 can be deflectable with respect to the seat 42. In this regard, it should be appreciated that the displaceable members 36 can be referred to as spring members. The stem 44 can extend proximally from the seat 42 as illustrated in FIG. 5C. Alternatively, the stem 44 can extend distally from the seat 42.

The torque transfer assembly 24 further includes a deformable gasket 48 that is disposed in the gap 38. Thus, the deformable gasket is disposed between the displaceable members 36 and the hub 34. For instance, the deformable gasket can be disposed adjacent both the displaceable members 36 and the hub 34. The deformable gasket 48 is thus separate from the displaceable members 36 and can have a material hardness that is different than the material hardness of at least one up to all of the displaceable members 36. For instance, the material hardness of the deformable gasket 48 can be less than the material hardness of at least one up to all of the displaceable members 36. Thus, the deformable gasket 48 can also be separate from the hub 34. Further, the material hardness of the deformable gasket 48 can be less than the material hardness of the hub 34. It should be appreciated that, for instance where the hub is separate from the displaceable members 36 but rotatably coupled to the displaceable members, that the deformable gasket can be monolithic with the hub 34 or attached to the hub 34 as desired. The deformable gasket 48 can define a radially inner surface 48a that faces the hub 34. The deformable gasket 48 can define a radially outer surface 48b that faces the displaceable members 36. The deformable gasket 48 can be made of any suitable material such that the displaceable members 36 are configured to apply a force to the outer surface 48b of the deformable gasket 48 that is sufficient to cause the outer surface 48b to displace radially inward along a direction toward the axis 32. The deformable gasket 48 can be an elastomer or made from any suitable alternative material. In accordance with one embodiment, the deformable gasket 48 is elastically deformable, such that the outer surface 48b moves from an initial position to a radially inward position in response to a biasing force from the displaceable members 36, and returns substantially to the initial position when the biasing force from the displaceable members 36 is removed. Thus, it can be said that the deformable gasket 48 can be an elastomer that compresses when the displaceable members 36 apply a radially inward force to the deformable gasket 48 toward the axis 32.

Figure 3:
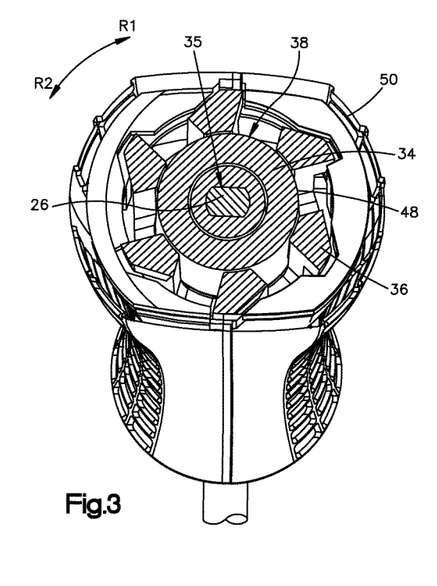
FIG. 3 is a sectional perspective view of a portion of the torque limiting instrument illustrated in FIG. 1, showing a cover that surrounds the cap.

The torque transfer assembly 24 further includes a cover 50 that is rotatably coupled to the grip member 27. Thus, a torque applied to the grip member 27 about the axis 32 is similarly applied to the cover 50. When the shaft 34 has a load at the distal end 30 (for instance when the anchor 21 is supported by the distal end and engages the target location 23), the torque can be applied to the cover 50 with respect to the shaft 34. For instance, the handle 22 can include the cover 50 that is monolithic with the grip member 27.

Alternatively, the cover 50 can be rotatably coupled to the grip member 27 in any suitable embodiment as desired. For example, the cover 50 can be separate from and attached to the grip member 27. The cover 50 extends, for example extends circumferentially, about the displaceable members 36, such that the displaceable members 36 are disposed between the cover 50 and the deformable gasket 48. At least a portion of the cover 50 can be disposed radially outward with respect to the displaceable members.

Figure 4A:
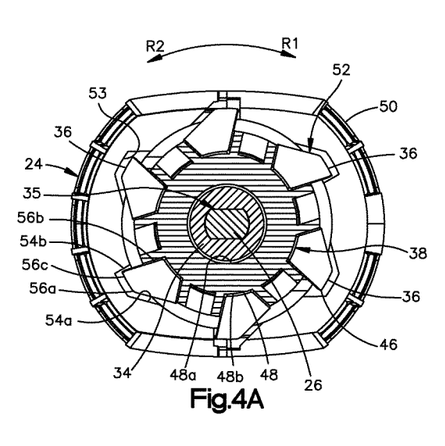
FIG. 4A is a sectional top plan view of the portion of the torque limiting instrument illustrated in FIG. 3.

During operation, a torque can be applied to the grip member 27, and thus to the cover 50. Application of the torque to the cover in a first direction of rotation R1 causes the cover 50 to bias the displaceable members 36 radially inward against the deformable gasket 48. The displaceable members 36 thus bias the deformable gasket 48, and in particular the outer surface 48*b* of the deformable gasket 48, to displace radially inwardly from the initial position to the radially inward position. As the deformable gasket 48 deforms radially inwardly, the biasing force from the cover 50 causes the displaceable members 36 to become displaced from the cover 50 along the radially inward direction. At the same time, the applied torque R1 in the first direction of rotation R1 causes the cover 50 to drive the displaceable members 36 to rotate in the first direction of rotation R1 until the torque reaches a predetermined threshold. Because the hub 34 is rotatably coupled to the displaceable members, and because the shaft 26 is rotatably coupled to the hub 34, rotation of the displaceable members 36 in the first direction of rotation R1 drives the shaft 26 to rotate in the first direction of rotation R1. The first direction of rotation R1 can be a clockwise direction of rotation that is configured to drive the anchor 21 into the target location 23.

When the torque reaches the predetermined threshold, the displaceable member 36 causes the deformable gasket 48 to deform radially inward a sufficient distance such that the displaceable members 36 become displaced from the cover 50 a sufficient distance that the cover 50 rotates in the first direction R1 with respect to the displaceable members 36. Thus, it can be said that the cover 50 is rotatably coupled to the displaceable members 36 with respect to the first direction of rotation R1 until the torque reaches the predetermined threshold, at which point deformation of the deformable gasket 48 causes the cover 50 to become rotatably decoupled from the displaceable members 36 in the first direction of rotation R1. When the cover 50 is rotatably decoupled from the displaceable members 36, the cover 50 is rotatable about the displaceable members 36 in the first direction of rotation R1. Thus, rotation of the cover 50 in the first direction of rotation R1 does not cause the shaft 26 to rotate in the first direction of rotation R1. For instance, the deformable gasket 48 can elastically deform toward the axis 32 as the cover 50 biases the displaceable members 36 against the deformable gasket 48. It should be appreciated that the cover 50 can bias the displaceable members 36 directly or indirectly against the deformable gasket 48. Furthermore, it should be appreciated that the displaceable members 36 can bias the deformable gasket 48 to deform directly or indirectly. The deformable gasket 48 can compress against the hub 34 in response to the biasing force applied to the deformable gasket 48 in the radially inward direction.

The cover 50 defines an inner surface 51, and at least one pocket 52 that extends radially outward into the inner surface 51 and terminates at an end 53. The at least one pocket 52 can be sized and configured to receive the at least one displaceable member 36. For instance, the cover 50 can define a plurality of pockets 52 that are sized and configured to receive respective ones of the displaceable members 36. For instance, the pockets 52 can be sized and configured to receive the engagement members 46 of the respective ones of the displaceable members 36. Adjacent ones of the displaceable members 36 can be spaced circumferentially equidistantly from each other or variably from each other. The seat 42 can further extend radially outward from the stem 44, such that the cover 50 rests against the seat 42 when the pockets 52 receive the respective displaceable members 36. As will now be described, the cover 50 and the engagement members 46 are dimensioned such that the cover 50 biases the displaceable members 36 radially inward as a torque is applied to the cover 50 in the first direction of rotation R1. Accordingly, the pockets 52 receive the respective ones of the displaceable members 36 when the applied torque is below the predetermined threshold, and eject the respective ones of the displaceable members 36 when the applied torque reaches the predetermined threshold.

For instance, with continuing reference to FIGS. 1-4A, each of the pockets 52 is at least partially defined by a respective first leading surface 54*a* and a first trailing surface 54*a* that is spaced from the first leading surface 54*a* along the first direction of rotation R1. Similarly, each of the displaceable members 36, and in particular the engagement members 46, defines a second leading surface 56*a* and a second trailing surface 56*b* that is spaced from the second leading surface 56*a* along the direction of rotation R1. Each of the first and second leading surfaces 54*a* and 56*a* are inclined in the first direction of rotation R1 as they extend radially out with respect to the axis 32. It should be appreciated that each of the first and second leading surfaces 54*a* and 56*a* can be straight, curved or otherwise suitably shaped as desired. The first and second leading surfaces 54*a* and 56*a* can correspond with each other in shape, such that the first and second leading surfaces 54*a* and 56*a* are in surface contact with each other in the pocket 52, though the first and second leading surfaces 54*a* and 56*a* can define any suitable alternative contact characteristics as desired. The first and second leading surfaces 54*a* and 56*a* can define any suitable angle A (see FIG. 5B) with respect to a straight radial line 61 that is perpendicular to the axis 32 and extends through the axis 32.

During operation, when the torque is applied to the cover 50 in the first direction of rotation R1, the first leading surfaces 54*a* bias the respective one of the displaceable members 36 against the deformable gasket 48. For instance, as the cover 50 is driven to rotate in the first direction of rotation R1, the first leading surfaces 54*a* ride along the second leading surfaces 56*a*, which urges the displaceable members 36 radially inward toward the axis 32, thereby causing the displaceable members 36 to compress the deformable gasket 48. Accordingly, the deformable gasket 48 compresses in response to the applied torque in the first direction of rotation R1. As a result, the first leading surfaces 54*a* ride along the displaceable members 36, and in particular the second leading surfaces 56*a*, radially inward as the applied torque increases in the first direction of rotation R1. When the applied torque reaches the predetermined threshold, the deformable gasket 48 deforms toward the axis 32 a sufficient distance in response to the applied torque until the displaceable members 36 travel out of the respective pockets 52. Otherwise stated, the second leading surfaces 56*a* engage respective ones of the plurality of first leading surfaces 54*a*, such that when the torque is below the predetermined threshold in the first direction of rotation R1, the first and second leading surfaces 54*a* and 56*a* engage so drive the displaceable members 36 to rotate in the first direction of rotation R1 only until the torque reaches the predetermined threshold, at which point the cover 50 rotates in the first direction R1 relative to the plurality of displaceable members 36. Thus, the first and second leading surfaces 54a and 56a are in abutment with each other when the applied torque in the first direction of rotation R1 is below the predetermined threshold, and are removed from abutment with each other when the applied torque in the first direction of rotation R1 reaches the predetermined threshold.

As the cover 50 rotates about the displaceable members 36, the deformable gasket 48 can urge an outer end 56c of the displaceable members 36 to ride along the inner surface 51 of the cover 50. The outer end 56c of each displaceable member 36 extends between the second leading surface 56a and the second trailing surface 56b. Further, the deformable gasket 48 can urge the displaceable members 36 into an adjacent pocket 52 as the cover 50 rotates about the displaceable members 36 until the leading surface 54a of the adjacent pockets 52 causes ejection of the displaceable members 36 from the adjacent pockets 52 as described above. Each instance that the displaceable members 36 are urged into sequentially adjacent pocket 52, contact between the displaceable members 36 and the cover 50 emits an audible "click" sound. Further, the user manually grasping the grip member 27 can feel differences in resistance of the handle 22 in response to the applied torque each instance that the displaceable members 36 are urged into sequentially adjacent pocket 52. Accordingly, the instrument 20 can provide both tactile and acoustic feedback that the torque applied to the grip member 27 in the first direction of rotation R1 has reached the predetermined threshold.

It should be appreciated that the torque transfer assembly 24 can include a first portion, for instance the cover 50, that is rotatably fixed with respect to the grip member 27. The torque transfer assembly 24 can further include a second portion that is rotatably fixed with respect to the shaft 26. The second portion of the torque transfer assembly 24 can include the hub 34, the deformable gasket 48, and the displaceable members 36. In this regard, the deformable gasket 48 applies a force that rotatably couples the second portion of the torque transfer assembly 24 to the first portion of the torque transfer assembly 24 when the torque is applied to the grip member 27 that is below a predetermined threshold in a first direction of rotation R1. For instance, the deformable gasket 48 can urge the displaceable members 36 to remain in the respective pockets 52 when the torque applied to the grip member 27 in the first direction of rotation R1 is below the predetermined threshold. The force applied by the gasket can be removed so as to decouple the second portion of the torque transfer assembly 24 from the first portion of the torque transfer assembly 24 when the applied torque reaches the predetermined threshold. For instance, as described above, the cover 50 can bias the displaceable members 36 to move out of the respective pockets against the force applied by the deformable gasket 48.

Because the torque transfer assembly 24 rotatably decouples the grip member 27 from the shaft 26 when the applied torque in the first direction of rotation R1 reaches the predetermined threshold, the instrument 20 can drive a plurality of anchors 21 into respective target locations 23 with the same maximum amount of torque.

It is recognized that circumstances can make it desirable to remove an inserted anchor 21 from the respective target location 23. Thus, while the instrument 20 has been described as coupling the handle 22 to the shaft 26 only so long as the applied torque in the first direction of rotation is below the predetermined threshold, the handle 22 can be fixedly rotatable coupled to the shaft 26 with respect to a torque that is applied to the handle 22 in a second direction of rotation R2 that is opposite the first direction of rotation R1. Thus, the second direction of rotation R2 can be a counterclockwise direction.

For instance, at least one or both of the first and second trailing surfaces 54b and 56b can have at least a portion up to an entirety that is not inclined in the second direction of rotation R2 as it extends radially out with respect to the axis 32. Accordingly, the cover 50 is fixedly coupled to the displaceable members 36 with respect to rotation in the second direction of rotation R2. For instance, at least a portion up to an entirety of at least one or both of the first and second trailing surfaces 54b and 56b can be perpendicular to the axis 32 and extend through the axis 32. Alternatively, at least a portion up to an entirety of at least one or both of the first and second trailing surfaces 54b and 56b can be inclined along the first direction of rotation R1 as they extend radially outward with respect to the axis 32. The at least a portion up to an entirety of at least one or both of the first and second trailing surfaces 54b and 56b can contact the other of the first and second trailing surfaces 54b and 56b in response to a torque applied to the cover 50 in the second direction of rotation R2, such that the. As described above, the torque applied to the grip member 27 in the second direction of rotation R2 is transferred to the cover 50.

During operation, when a torque is applied to the cover 50 in the second direction of rotation R2, the first trailing surfaces 54b apply a force to the respective second trailing surfaces 56b that urges the second trailing surfaces 56b, and thus the corresponding displaceable members 36, to rotate in the second direction R2. Because the displaceable members 36 are rotatably coupled to the hub 34, and the hub is rotatably coupled to the shaft 26, rotation of the displaceable members 36 in the second direction of rotation R2 causes the shaft 26 to rotate in the second direction of rotation R2. Further, as the cover is biased by the applied torque to rotate in the second direction of rotation R2, the first trailing surface 54b does not apply a radially inward force to the second trailing surface 56b. Thus, the cover 50 does not bias the displaceable members 36 against the compressible gasket 48 in response to the applied torque in the second direction of rotation R2.

Figure 4B:
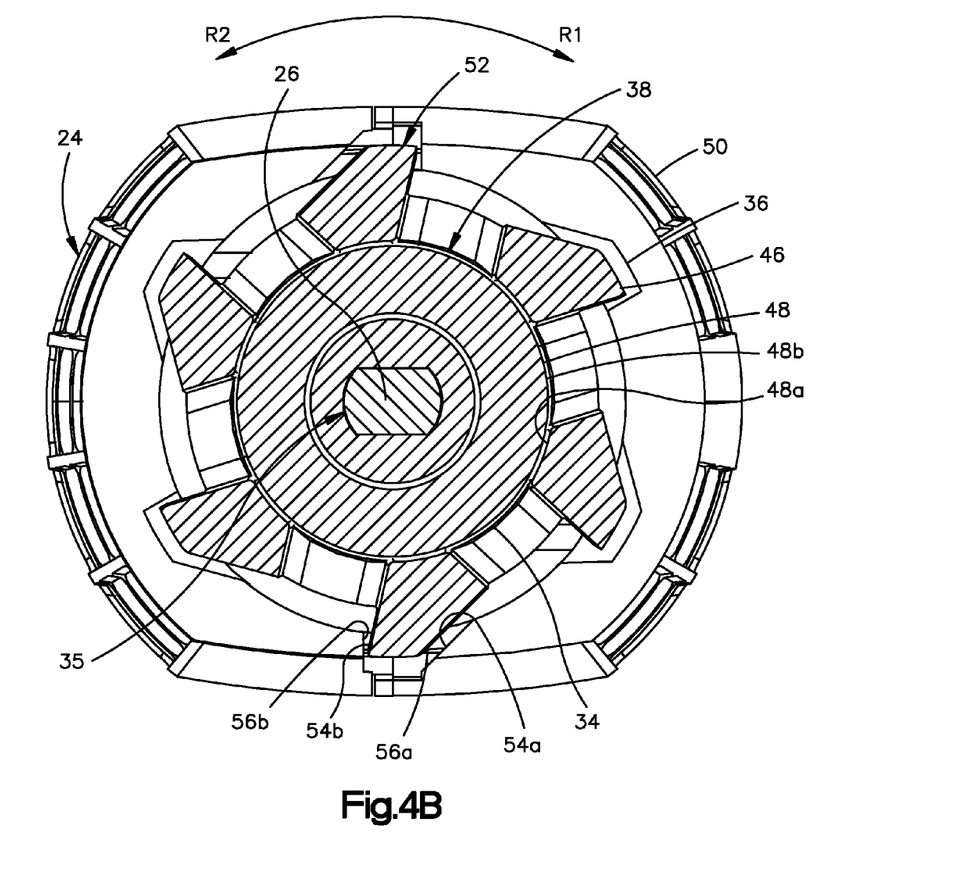
FIG. 4B is a sectional top plan view of the portion of the torque limiting instrument as illustrated in FIG. 4A, but constructed in accordance with an alternative embodiment.

Alternatively, as illustrated in FIG. 4B, in accordance with one example, it is recognized that it may be desired to limit the torque applied to the shaft in the second direction of rotation R2. For instance, when removing an anchor from a target location, it may be desired to limit the amount of torque applied to the head of the anchor. Thus, in one example of the instrument 20, each of the first and second trailing surfaces 54b and 56b can be inclined in the second direction of rotation R2 as they extend radially out with respect to the axis 32. It should be appreciated that each of the first and second trailing surfaces 54b and 56b can be straight, curved or otherwise suitably shaped as desired. The first and second trailing surfaces 54b and 56b can correspond with each other in shape, such that the first and second trailing surfaces 54b and 56b are in surface contact with each other in the pocket 52, though the first and second trailing surfaces 54b and 56b can define any suitable alternative contact characteristics as desired. The first and second trailing surfaces 54b and 56b can define any suitable angle with respect to a straight radial line that is perpendicular to the axis 32 and extends through the axis 32.

Thus, during operation of the instrument as illustrated in FIG. 4B, when the torque is applied to the cover 50 in the second direction of rotation R2, the first trailing surfaces 54b bias the respective one of the displaceable members 36 against the deformable gasket 48. For instance, as the cover 50 is driven to rotate in the second direction of rotation R2, the first trailing surfaces 54b ride along the second trailing surfaces 56b, which urges the displaceable members 36 radially inward toward the axis 32, thereby causing the displaceable members 36 to compress the deformable gasket 48. Accordingly, the deformable gasket 48 compresses in response to the applied torque in the second direction of rotation R2. As a result, the first trailing surfaces 54b ride along the displaceable members 36, and in particular the second trailing surfaces 56b, radially inward as the applied torque increases in the second direction of rotation R2.

When the applied torque reaches a second predetermined threshold, the deformable gasket 48 deforms toward the axis 32 a sufficient distance in response to the applied torque until the displaceable members 36 travel out of the respective pockets 52. Otherwise stated, the second trailing surfaces 56b engage respective ones of the plurality of first trailing surfaces 54b, such that when the torque is below the second predetermined threshold in the second direction of rotation R2, the first and second trailing surfaces 54b and 56b engage so drive the displaceable members 36 to rotate in the second direction of rotation R2 only until the torque reaches the predetermined threshold, at which point the cover 50 rotates in the second direction of rotation R2 relative to the plurality of displaceable members 36. Thus, the first and second trailing surfaces 54b and 56b can be in abutment with each other when the applied torque in the second direction of rotation R2 is below the second predetermined threshold, and are removed from abutment with each other when the applied torque in the second direction of rotation R2 reaches the second predetermined threshold. The angle of the first and second trailing surfaces 54b and 56b can be equal to, greater than, or less than the angle of the first and second leading surfaces 54a and 56a. Accordingly, the second predetermined threshold can be equal to, greater than, or less than the predetermined threshold in the first direction of rotation R1.

A method of fabricating the instrument 20 can include the step of fixing the plurality of displaceable members 36 with respect to the shaft 26 so that the plurality of displaceable members 36 are rotatably fixed to the shaft 26. For instance, the method can include the step of rotatably fixing the hub 34 to the shaft 26. The step of rotatably fixing can be performed while the displaceable members 36 are rotatably fixed to the hub 34. The method can further include the step of placing the deformable gasket 48 between the displaceable members 36 and the hub 34. For instance, the method can include step coupling the steps of inserting the shaft 26 into the aperture 35 defined by the hub 34. The method can further include the step of placing the cover 50 about the displaceable members 36 such that the displaceable members 36, and in particular the engagement members 46, are disposed in respective ones of the pockets 52.

Figure 6A:
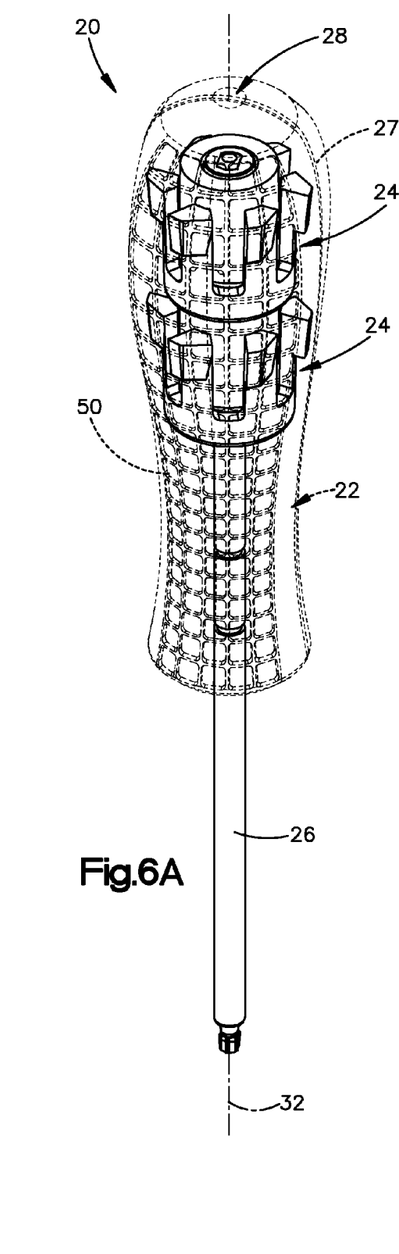
FIG. 6A is a perspective view of a torque limiting instrument similar to FIG. 1, but shown constructed in accordance with an alternative embodiment.
Figure 6B:
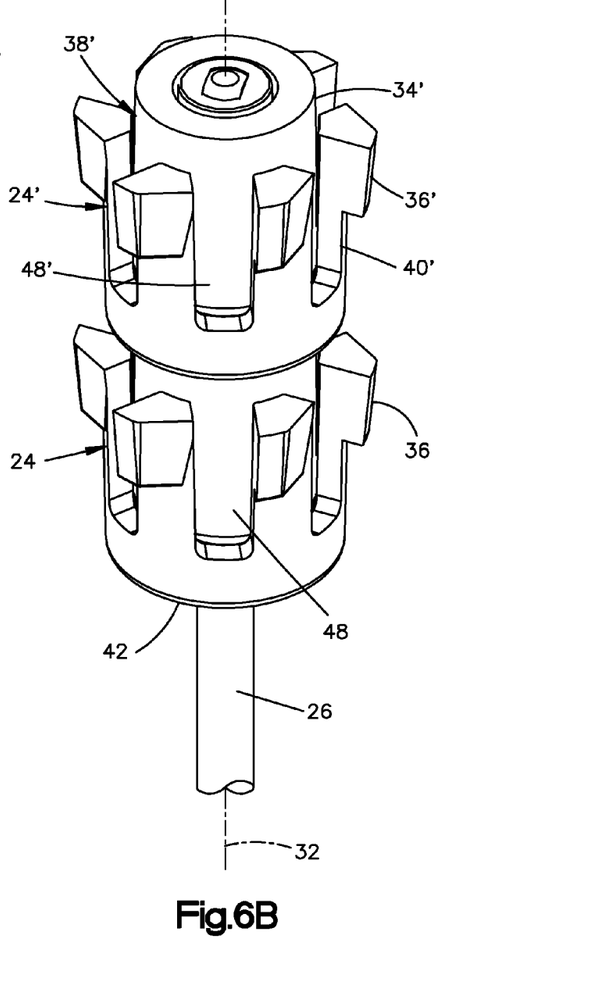
FIG. 6B is a perspective view of a portion of the torque limiting instrument illustrated in FIG. 6A.

Referring now to FIGS. 6A-6B, it should be appreciated that the instrument 20 can include as many torque transfer assemblies 24 spaced along the shaft 26, and thus along the axis 32, as desired. For instance, FIGS. 6A-6B illustrate a second torque transfer assembly 24' constructed as described above with respect to the first torque transfer assembly 24. Thus, the second torque transfer assembly 24' can include a second hub 34' rotatably fixed with respect to the shaft 26 and disposed adjacent the first hub 34 along the axis 32. The second torque transfer assembly 24' includes a plurality of second displaceable members 36' spaced radially outward with respect to the second hub 34' so as to define a second gap 38' between the second hub 34' and the second displaceable members 36'. The second displaceable members 36' are rotatably fixed with respect to the second hub 34'. The cover 50 extends about the second displaceable members 36' as described above with respect to the first displaceable members 36. The second torque transfer assembly 24' can include a second deformable gasket 48' disposed in the second gap 38'. The second displaceable member 36' is thus disposed between the cover 50 and the second deformable gasket 48'. It should be appreciated that the seat 42 of the distal most one of the torque transfer assemblies 24 can extend radially out from the respective stems 44, while the seats 42 of the torque transfer assemblies 24 spaced proximal with respect to the distal most one of the torque transfer assemblies 24 do not extend radially out from the respective stems 44, thereby allowing the cover 50 to pass over those seats 42 and rest against the seat 42 of the distal most one of the torque transfer assemblies 24. Application of the torque to the cover 50 in the first direction of rotation R1 causes the cover 50 to bias the second displaceable members 36' against the second deformable gasket 48', and also causes the cover 50 to drive the second displaceable members 36' to rotate in the first direction of rotation R1 until the torque reaches the predetermined threshold, at which point the second displaceable members 36' causes the second deformable gasket 48' to deform a sufficient amount such that the second displaceable members 36' becomes displaced from the cover 50 so that the cover 50 rotates in the first direction of rotation R1 with respect to the second displaceable members 36'.

It is appreciated that a method can be provided for operating the instrument 20 as described above. For instance, the method can include the step of applying a torque to the cover 50 in the first direction of rotation R1 and, in response thereto, causing the cover 50 to urge the displaceable members 36 to rotate in the first direction R1 while the compressible gasket 48 applies a force to the displaceable members 36 that causes the displaceable members 36 to be rotatably coupled to the cover. The method can include the step of applying the torque at the predetermined threshold and, in response thereto, causing the cover 50 to bias the displaceable members 36 toward the shaft 24 against the force of the compressible gasket 48 a sufficient distance so that the cover 50 is rotatably decoupled from the displaceable members 36. The method can then include the step of rotating the cover 50 relative to the displaceable members 36 in the first direction of rotation.

Figure 5A:
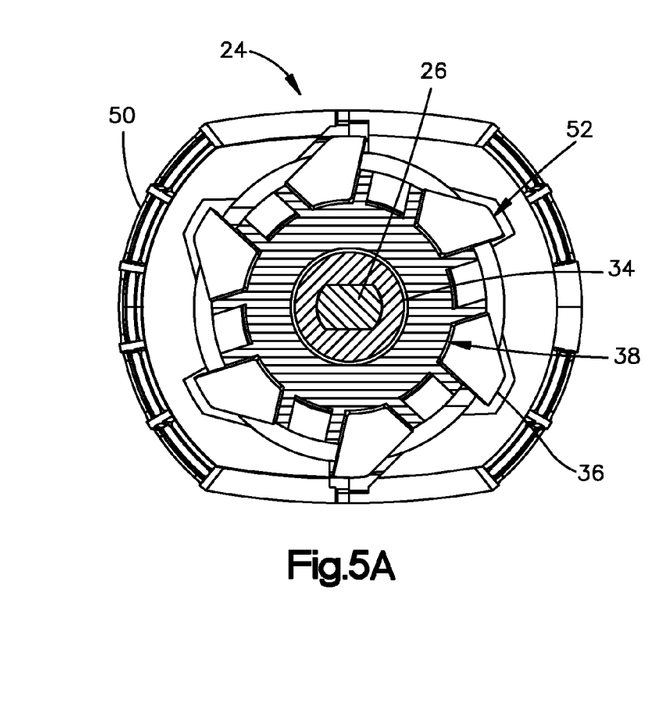
FIG. 5A is a sectional top plan view of the portion of the torque limiting instrument illustrated in FIG. 4A, showing various dimensional information.
Figure 5B:
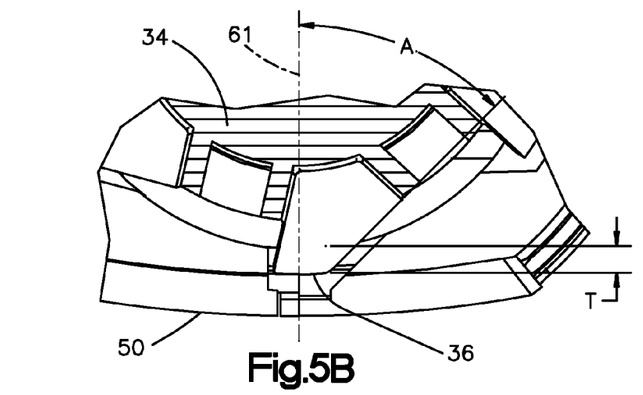
FIG. 5B is an enlarged portion of the torque limiting instrument illustrated in FIG. 5A, showing various additional dimensional information.
Figure 5C:
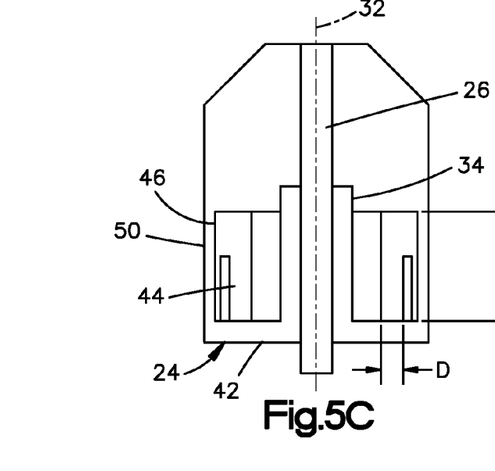
FIG. 5C is a sectional side elevation view of a portion of the torque limiting instrument illustrated in FIG. 4A, showing various additional dimensional information.

Referring now to FIGS. 5A-5C, the instrument 20 can define a number of dimensions. For instance, as illustrated in FIG. 5A, the cover 50 can define a first outer cross-sectional dimension D1 along a straight radial line that is perpendicular to the axis 32 and intersects the axis 32. The inner surface 51 of the cover 50 can define second outer cross-sectional dimension D2 along the straight radial line that is perpendicular to the axis 32 and intersects the axis 32. The compressible gasket 48 can define a third outer cross-sectional dimension D3 along the straight radial line that is perpendicular to the axis 32 and intersects the axis 32. The hub 34 can define a fourth outer cross-sectional dimension D4 along the straight radial line that is perpendicular to the axis 32 and intersects the axis 32. The first, second, third, and fourth cross-sectional dimensions D1, D2, D3, and D4, can be diameters or alternatively shaped cross-sections as desired. It should be further appreciated that the first, second, third, and fourth cross-sectional dimensions D1, D2, D3, and D4 can be dimensioned as desired. In accordance with the illustrated embodiment, the first cross-sectional dimension D1 is greater than the second cross-sectional dimension D2, the second cross-sectional dimension D2 is greater than the third cross-sectional dimension D3, and the third cross-sectional dimension D3 is greater than the fourth cross-sectional dimension D4.

Referring to FIG. 5B, each of the displaceable members 36, and in particular the engagement members 46, can extend into the respective pockets 52 at a depth T. The depth T can be measured from a first straight line to a second straight line that is parallel to the first straight line. The first and second straight lines extend perpendicular to the straight radial line 61. The first straight line extends through a junction between the inner surface 51 of the cover 50 and the first leading surface 54a, and the second straight line is disposed at the end 53 of the pocket 52. FIG. 5B further illustrates the angle A described above. The depth T and angle A can be any dimension as desired.

Referring to FIG. 5C, the stem 44 of the displaceable members 36 defines a radial thickness B. Further, the displaceable members 36 define a height H that extends from the seat 42 along a direction parallel to the axis 32. The radial thickness B and the height H can be any dimensions as desired.

The instrument 20 was tested with the following dimensions: D1=38 mm, D2=34 mm, D3=22 mm, D4=14 mm, H=18 m, T=1.5 mm, B=3 mm, and A=45 degrees. The instrument 20 was tested both with a single torque transfer assembly 24 ("Design Single") and with serial torque transfer assemblies 24 adjacent each other along the shaft 26 ("Design Serial"). The instrument 20 was also tested with the deformable gasket 48 or gaskets 48 and 48' made from rubber made of Polyurethane manufactured by vacuum casting, and deformable gasket 48 or gaskets 48 and 48' manufactured by selective laser sintering (SLS). The test results are illustrated below at Table 1, where hardness values including the letter "B" indicates that the gasket 48 was made of Polyurethan manufactured by vacuum casting. Hardness values without the letter "B" indicate that the gasket 48 was manufactured by Selective Laser Sintering (SLS).

TABLE 1

| Test Variation | Shore Hardness | | | Amount of Clicks | Torque Moment | | |
|---|---|---|---|---|---|---|---|
| Design Single | 00 | 50 | 60 | 0-20 | 1.1 | 2.3 | 2.3 |
|  | 70 | 80 | 90 | 0-20 | 2.88 | 3.30 | 6.2 |
|  |  | 95 |  | 0-20 |  | 8 |  |
| Design Single | 50 | 60 | 70 | 0-20 | 2.32 | 2.28 | 2.49 |
|  | 85 B | 90 B | 95 B | 0-20 | 4.15 | 5.74 | 7.57 |
|  |  | 100 B |  | 0-20 |  | 10.58 |  |
| Design Serial | 50 | 60 | 70 | 0-20 | 3.9 | 4.2 | 4.6 |
|  | 80 | 90 B |  | 0-20 | 5.5 | 10.7 |  |

In this regard, it should be appreciated that the predetermined threshold can be at least partially determined by a number of factors. For instance, the angle A between the first and second leading surfaces 54a and 56a and the straight radial line that is perpendicular to the axis 32 and extends through the axis 32 can at least partially determine the predetermined threshold. For example, increasing the angle A can cause the predetermined threshold to increase. Furthermore the depth of the pockets 52 along the radial direction can at least partially determine the predetermined threshold. For example, increasing the depth can cause the predetermined threshold to increase. Further, the gasket 48 can have a compressibility in response to an applied force that can at least partially determine the predetermined threshold. For example, the gasket 48 can have a hardness in response to an applied force that at least partially determines the predetermined threshold. For example, decreasing compressibility, or increasing hardness, can increase the predetermined threshold. Furthermore, the number of displaceable members 36 can at least partially determine the predetermined threshold. For example, increasing numbers of displaceable members 36 can increase the predetermined threshold. Furthermore, the spring constant of the displaceable members 36 can at least partially determine the predetermined threshold. For example, higher spring constants can increase the predetermined threshold. Further, the predetermined threshold can be at least partially determined by the first, second, third, and fourth cross-sectional dimensions D1, D2, D3, and D4, the depth T, the radial thickness B, and the height H, both alone and in combination with each other. Thus, a kit of instruments 20 can be provided, each having different predetermined thresholds. A bone fixation assembly can include one or more of the instruments 20 of the kit of instruments 20, one or more anchors 23, alone or in combination with one or more surgical implants.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should further be appreciated that the various alternative embodiments described above with respect to one illustrated embodiment can apply to all embodiments as described herein, unless otherwise indicated.

What is claimed is:

1. A torque limiting instrument comprising:
a shaft having a driving end;
a displaceable member disposed radially out from the shaft and rotatably fixed to the shaft,
a deformable gasket disposed between the shaft and the displaceable member; and
a cover that extends about the displaceable member such that the displaceable member is disposed between the cover and the deformable gasket,
wherein the cover is rotatably coupled to the displaceable member until a torque applied to the cover in a first direction of rotation reaches a predetermined threshold, at which point the cover causes the displaceable member to bias the deformable gasket to deform a sufficient distance such that the cover becomes rotatably decoupled from the displaceable member in the first direction of rotation.

2. The torque limiting instrument as recited in claim 1, wherein the cover defines a pocket that receives the displaceable member when the applied torque force is below the predetermined threshold.

3. The torque limiting instrument as recited in claim 2, wherein the cover includes a first leading surface that partially defines the pocket and the displaceable member includes a second leading surface, each of the first and second leading surfaces inclined in the first direction of rotation as they extend radially out with respect to a central axis of the shaft.

4. The torque limiting instrument as recited in claim 3, wherein the first leading surface biases the displaceable member against the deformable gasket in response to the applied torque, and the deformable gasket deforms toward the central axis a sufficient distance so as to allows the displaceable member to travel out of the pocket when the torque reaches the predetermined threshold.

5. The torque limiting instrument as recited in claim 4, wherein as the applied torque increases, the applied torque causes the first leading surface to ride along the second leading surface so as to bias the displaceable member toward the axis.

6. The torque limiting instrument as recited in claim 1, wherein the deformable gasket elastically deforms toward a central axis of the shaft as the cover biases the displaceable member against the deformable gasket.

7. The torque limiting instrument as recited in claim 1, wherein the deformable gasket comprises an elastomer that compresses when the cover biases the displaceable member against the deformable gasket in response to the applied torque in the first direction of rotation.

8. The torque limiting instrument as recited in claim 1, wherein the cover defines a first trailing surface and the displaceable member defines a second trailing surface that abuts the first trailing surface, such that when a torque is applied to the cover in a second direction opposite the first direction, the cover causes the displaceable member to rotate in the second direction of rotation.

9. The torque limiting instrument as recited in claim 8, wherein both of the first and second trailing surfaces have at least a portion that is inclined in the first direction of rotation as they extend radially out with respect to the central axis.

10. The torque limiting instrument as recited in claim 9, wherein both of the first and second trailing surfaces extend radially with respect to the central axis along a direction that is perpendicular to the central axis.

11. The torque limiting instrument as recited in claim 1, wherein the cover is rotatably coupled to the displaceable member until a torque applied to the cover in a second direction of rotation opposite the first direction of rotation reaches a predetermined threshold, at which point the cover causes the displaceable member to bias the deformable gasket to deform a sufficient distance such that the cover becomes rotatably decoupled from the displaceable member in the second direction of rotation.

12. The torque limiting instrument as recited in claim 11, wherein the cover defines a first trailing surface and the displaceable member defines a second trailing surface that abuts the first trailing surface, wherein each of the first and second trailing surfaces are inclined in the second direction of rotation as they extend radially out with respect to a central axis of the shaft.

13. The torque limiting instrument as recited in claim 1, further comprising a hub that is rotatably coupled to the shaft, wherein the displaceable member extends radially outward with respect to the hub so as to define a gap between the hub and the displaceable member, and the deformable gasket is disposed in the gap.

14. The torque limiting instrument as recited in claim 13, wherein the hub is rotatably fixed to the displacement member.

15. The torque limiting instrument as recited in claim 1, wherein the cover defines a plurality of first leading surfaces, the torque limiting instrument further comprising a plurality of displaceable members that define respective second leading surfaces that engage respective ones of the plurality of first leading surfaces, such that when the applied torque in the first direction of rotation is below the predetermined threshold, the second leading surfaces of the plurality of displaceable members engage respective ones of the first leading surfaces such that the cover drives the plurality of displaceable members to rotate in the first direction of rotation only until the applied torque in the first direction of rotation reaches the predetermined threshold, at which point the cover rotates in the first direction of rotation relative to the plurality of displaceable members.

16. The torque limiting instrument as recited in claim 15, wherein the deformable gasket compresses against the hub.

17. The torque limiting instrument as recited in claim 15, wherein the displaceable member comprises a spring member that is elastically deflectable with respect to the hub.

18. The torque limiting instrument as recited in claim 1, wherein the displaceable member is a first displaceable member and the deformable gasket is a first deformable gasket, the torque limiting instrument further comprising:
  a second displaceable member disposed adjacent the first displaceable member along the axis, the second displaceable member further disposed radially out from the shaft and rotatably fixed to the shaft;
  a second deformable gasket disposed adjacent the first deformable gasket along the axis, the second deformable gasket further disposed between the shaft and the second displaceable member, such that the second displaceable member is disposed between the cover and the second deformable gasket,
  wherein the cover is rotatably coupled to the second displaceable member until the torque applied to the cover in a first direction of rotation reaches the predetermined threshold, at which point the cover causes the second displaceable member to bias the deformable gasket to deform a sufficient distance such that the cover becomes rotatably decoupled from the second displaceable member in the first direction of rotation.

19. A torque limiting instrument comprising:
  a grip member
  a shaft having a driving end;
  a torque transfer assembly having a first portion rotatably fixed with respect to the grip member, and a second portion including a gasket rotatably fixed with respect to the shaft,
  wherein the second portion includes a deformable gasket that provides a force that rotatably couples the second portion to the first portion when a torque applied to the grip member in a first direction of rotation is below a predetermined threshold, and decouples the second portion from the first portion when the applied torque reaches the predetermined threshold.

20. The torque limiting instrument as recited in claim 19, wherein the second portion is rotatably fixed to the first portion when a torque is applied to the grip member in a second direction of rotation that is opposite the first direction of rotation.

* * * * *